United States Patent
Chaudhary et al.

(10) Patent No.: US 11,104,640 B2
(45) Date of Patent: Aug. 31, 2021

(54) PROCESS FOR PREPARATION OF STABLE DIANIONIC COMPLEX USEFUL IN DESIGNING THE WHITE LIGHT EMITTING DEVICES

(71) Applicant: COUNCIL OF SCIENTIFIC AND INDUSTRIAL RESEARCH, New Delhi (IN)

(72) Inventors: Yatendra Singh Chaudhary, Odisha (IN); Biswajit Mishra, Odisha (IN); Surjendu Bhattacharyya, Odisha (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 274 days.

(21) Appl. No.: 16/298,201

(22) Filed: Mar. 11, 2019

(65) Prior Publication Data

US 2019/0276390 A1    Sep. 12, 2019

(30) Foreign Application Priority Data

Mar. 9, 2018  (IN) .............................. 201811008726

(51) Int. Cl.
| | | |
|---|---|---|
| *C07C 253/30* | (2006.01) | |
| *C09K 11/06* | (2006.01) | |
| *C09K 11/02* | (2006.01) | |
| *H01F 1/01* | (2006.01) | |

(52) U.S. Cl.
CPC .......... *C07C 253/30* (2013.01); *C09K 11/025* (2013.01); *C09K 11/06* (2013.01); *C09K 2211/10* (2013.01); *H01F 1/01* (2013.01)

(58) Field of Classification Search
CPC ..... C09K 11/06; C09K 11/025; C09K 211/10; C07C 253/30
See application file for complete search history.

(56) References Cited

U.S. PATENT DOCUMENTS 3,201,399 A * 8/1965 Webster ................. C06B 43/00
                                                        544/351

OTHER PUBLICATIONS

Chang, R., "Dimerization of the Tetracyanoethylene Anion Radical", J. Phys. Chem., vol. 74, No. 9, Apr. 30, 1970, pp. 2029-2030.*

* cited by examiner

*Primary Examiner* — C Melissa Koslow
(74) *Attorney, Agent, or Firm* — BakerHostetler

(57) ABSTRACT

The present invention relates to the formation of a stable dianionic π-dimer-$[TCNE]_2^{2-}$ (TCNE-tetracyanoethylene) at ambient conditions that exhibits unusually intense white emission over the entire visible spectral range (400-800 nm) and has application in designing white light emitting devices. Particularly, the present invention relates to a process for the preparation of stable dimer in an organic solvent upon aging at room temperature, in the presence of anions such as Br−, Cl−, SCN−, which reduces the TCNE to a TCNE anion radical (TCNE.−) which subsequently dimerizes to form the stable dianionic dimer upon aging. More particularly, the dimer formed in this invention opens a new class of materials to design white light emitting devices having high intensity over the entire visible spectral range. The dimer also forms electron transfer salts used to develop new molecule-based metals, superconductors, and magnets.

4 Claims, 2 Drawing Sheets

PROCESS FOR PREPARATION OF STABLE DIANIONIC COMPLEX USEFUL IN DESIGNING THE WHITE LIGHT EMITTING DEVICES

CROSS REFERENCE TO RELATED APPLICATIONS

This application claims priority to Indian Patent Application No. 201811008726, filed on Mar. 9, 2018, the disclosure of which is incorporated by reference in its entirety.

FIELD OF THE INVENTION

The present invention relates to a process for the preparation of unconventional stable dianionic π-dimer-$[TCNE]_2^{2-}$ (TCNE=tetracyanoethylene) that forms under ambient conditions over a period of time and characterized by the highly sensitive steady state and time-resolved photoluminescence measurement and electrospray ionization mass spectrometry (ESI-MS).

Particularly, the present invention relates to a process for the preparation of dianionic dimer that exhibits unusually intense white emission with the chromaticity coordinates from 0.20, 0.27 to 0.3, 0.46, and has potential application in designing the white light emitting devices.

BACKGROUND OF THE INVENTION

The attractive interaction between two ions having similar charge (anions or cations) to form their dimer is contrary to our conventional understanding of Coulombic repulsion.

The privilege of the attractive over the repulsive forces in the overall stabilization of such complex is itself fascinating and properties arising from such unusual dimers can have vast technological implications. Furthermore, there is scarcely any single material that exhibit a broad emission over the visible spectrum, rather white LEDs available typically consist of a blue LED and one or more phosphors to convert part of the blue light to longer wavelengths and suffers from low spectral power distribution in the red region and dampening emission intensity (Pust, P., Schmidt, P. J. & Schnick, W. A revolution in lighting. *Nat. Mater.* 14, 454-458, 2015; US2016240781).

Early indication of dianionic dimer, e.g. i-$[TCNE]_2^{2-}$ (TCNE=tetracyanoethylene) in solid crystal formed under stringent conditions (at 77K) was perceived by the diamagnetic behavior (Chang, R. Dimerization of Tetracyanoethylene Anion Radical. *J. Phys. Chem.* 74, 1970, 2029-2030). The driving force for this is the attraction between counter ions assisted by dispersive interactions which help to surmount the internal Coulombic repulsive barrier (Yoldi et al, *J. Phys. Chem. A* 111, 8020-8027 (2007) and Casado et al *Angew. Chem. Int. Edit.* 52, 6421-6425 (2013). The privilege of the attractive over the repulsive forces in the overall stabilization of such complex is itself fascinating and properties arising from such unusual dimers can have vast technological implications (Chang, R. Dimerization of Tetracyanoethylene Anion Radical. *J. Phys. Chem.* 74, 1970, 2029-2030; Lu et al Stable (long-bonded) dimers via the quantitative self-association of different cationic, anionic, and uncharged π-radicals: structures, energetics, and optical transitions. *J. Am. Chem. Soc.* 125, 12161-12171, 2003; Fatila et al Anions stabilize each other inside macrocyclic hosts. *Angew. Chem. Int. Edit.* 55, 14057-14062, 2016). The existence of such an exotic dianionic dimer species from direct observation as a discreet entity in solution phase has not been established until the present investigation. $[TCNE]^{.-}$ can form electron transfer salts, therefore, it has tremendous potential in a number of crucial applications in molecule-based metals, superconductors, and magnets (Novoa et al. On the existence of long C—C bonds between pairs of anions which repel: when and why? A test case on the $[TCNE]_2^{2-}$ dimers found in ionic crystals. *CrystEngComm.* 4, 373-377, 2002; Exceptionally long (≥2.9 Å) C—C bonds between $[TCNE]^-$ ions: two-electron, four-center π*-π*C—C bonding in π-$[TCNE]_2^{2-}$. *Angew. Chem. Int. Edit.* 40, 2540-2545, 2001; Miller et al, Electron-transfer salts of 1,2,3,4,5-pentamethylferrocene, $Fe^{II}(C_5Me_5)(C_5H_5)$. Structure and magnetic properties of two 1:1 and two 2:3 $Fe(C_5Me_5)(C_5H_5)$ electron-transfer salts of tetracyanoethylene. *Inorg. Chem.* 40, 2058-2064, 2001). Therefore, it is critical to know exactly how two $[TCNE]^{.-}$ moieties interact in a single π-$[TCNE]_2^{2-}$ entity. This curiosity drove us to investigate concrete evidence for the presence of $[TCNE]_2^{2-}$ in the solution phase at room temperature.

OBJECTS OF THE INVENTION

The main object of the present invention is to provide a process for the preparation of stable dianionic π-dimer at ambient condition in solution.

Another object of the present invention is to provide unconventional stable dianionic dimer π-$[TCNE]_2^{2-}$ that forms at ambient condition in solution.

Yet another object of the present invention is to provide various organic solvents to form stable dianionic dimer π-$[TCNE]_2^{2-}$.

Yet another object of the present invention is to demonstrate the florescence property exhibited by the dianionic dimer using highly sensitive steady state and time-resolved photoluminescence spectroscopy as a tool.

Yet another object of the present invention is to provide a broad emission over the entire visible spectral range by the synthesized dimer.

Still another object of the present invention is to demonstrate the highly intense white light emission so that it is useful in designing the highly demanding white light emitting devices (W-LEDs, LED displays).

SUMMARY OF THE INVENTION

Accordingly, present invention provides a process for the preparation of stable dianionic dimer π-$[TCNE]_2^{2-}$ in solution state wherein TCNE=tetracyanoethylene and the said process comprising the steps of:
i. adding tetra cyanoethylene (TCNE) in a solvent to obtain TCNE solution with the weight ratio of 1:20 to 1:100;
ii. adding anion species source with the concentration range of 1:2 to 1.16 in a solvent to obtain anion stock solution;
iii. adding the solution as obtained in step (i) in the solution as obtained in step (ii) with the final concentration ratio of TCNE and anion species ranging from 3:1 to 27:1;
iv. ageing the solution as obtained in step (iii) for a period in the range of 20 hours to 30 days at room temperature in the range of 20 to 40° C. to obtain the stable dianionic dimer π-$[TCNE]_2^{2-}$.

In an embodiment of the present invention, wherein organic solvent used is selected from the group consisting of acetonitrile (ACTN), acetone and 2-methyl tetrahydrofuran (MTHF).

In another embodiment of the present invention, the anion species source is selected from the group consisting of tetra-n-butyl ammonium bromide [TBAB], cetyltrimethylammoniumbromide [CTAB], tetra-n-butyl ammonium chloride [TBAC] and ammonium thiocyanate.

In yet another embodiment of the present invention, stable dianionic complex $\pi$-[TCNE]$_2^{2-}$ as prepared by the process exhibits highly intense broad emission over the entire visible spectral range (400-800 nm), which further intensifies with aging time in the range of 20 hours to 30 days.

In yet another embodiment of the present invention, said dimer exhibits intense white light emission with the chromaticity coordinates ranging from 0.20, 0.27 to 0.3, 0.46, and is tunable by changing the organic solvents.

In yet another embodiment of the present invention, said dimer is useful to develop the white light emission devices.

In yet another embodiment of the present invention, said dimer forms electron transfer salts, therefore, it can form new molecule-based metals, superconductors, and magnets.

DETAILED DESCRIPTION OF THE INVENTION

Present invention provides a facile process for the formation of a stable dianionic $\pi$-dimer-[TCNE]$_2^{2-}$ (TCNE=tetracyanoethylene) at ambient conditions in solution. Stock solutions of TCNE were made in organic solvent (such as acetonitrile (ACTN), 2-methyltetrahydrofuran (MTHF) and acetone). Similarly, stock solutions of cetyltrimethylammoniumbromide (CTAB), tetra-n-butyl ammonium chloride (TBAC) and tetra-n-butyl ammonium bromide (TBAB) were prepared in organic solvent (eg. ACTN, MTHF and acetone) and added to the TCNE solutions in such a way that the final concentration of the TCNE was 3-7 mM and that for each of CTAB, TBAC and TBAB was 1-2 mM. The mixed solutions were allowed to age at room temperature. The aging time varied from 20 hours to 30 days in different sets of synthesis and temperature varied from 20 to 40° C. The formed dimer exhibits highly intense broad emission over the entire visible spectral range (400-800 nm) with the chromaticity coordinates ranging from 0.20, 0.27 to 0.3, 0.46 can be tuned by changing the organic solvents.

The present invention provides formation of stable dianionic dimer $\pi$-[TCNE]$_2^{2-}$ in solution state at room temperature, that forms by dispersion interactions induced dimerization of anionic radical [TCNE].$-$ in organic solvent, in the presence of anion species (Br$^-$, Cl$^-$, SCN$^-$).

The present invention provides a process for the single pot preparation of dianionic dimer-[TCNE]$_2^{2-}$ at ambient conditions by reacting TCNE with anions (Br–, Cl– and SCN–) dissolved in organic solvents (ACTN, MTHF and acetone) with different aging time [20 hours to 30 days] and also its detection by photoluminescence and ESI-MS under ambient conditions.

The anions are selected from the group comprising of Br–, Cl– and SCN– from TBAB, TBAC and ammonium thiocyanate, respectively.

Excitation wavelengths are chosen as 575, 575 and 482 nm for the selective detection of dianionic r-dimer-[TCNE]$_2^{2-}$ through photoluminescence at ambient in ACTN, MTHF and acetone, respectively.

ESI-MS measurements are performed in positive ion mode.

Highly intense broad emission over the entire visible spectral range (400-800 nm) of the dianionic dimer-[TCNE]$_2^{2-}$, which further intensifies with aging time (20 hours to 30 days).

Figure 1:
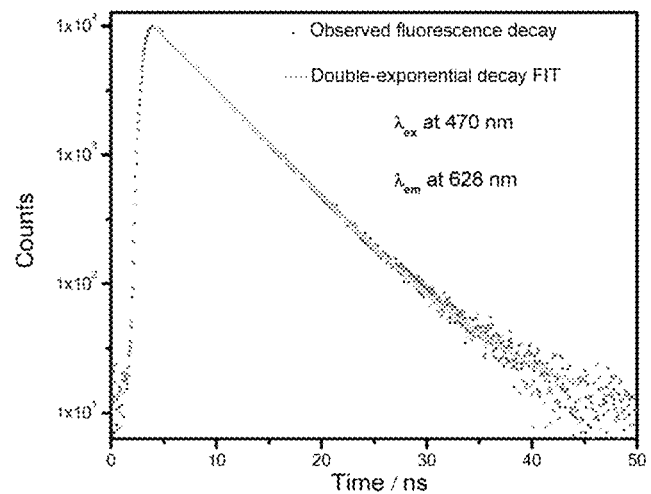
FIG. 1 represents time resolved fluorescence measurement. Fluorescence decay measured by time-correlated single photon counting (TCSPC) for [TCNE]$_2^{2-}$ after exciting at 470 nm while collecting the emission 628 nm. Observed data was obtained after averaging the fluorescence decay of TCNE+cetyltrimethylammonium bromide (CTAB) in acetonitrile (ACTN). A double-exponential decay ($\alpha_1$exp($-t/\tau_1$)+$\alpha_2$ exp($-t/\tau_2$)) FIT yields the lifetime decays $\tau_1$, and $\tau_2$ of about 5.15±0.01 ns ($\alpha_1$=99.85%), and 47.95±32.84 ns ($\alpha_2$=0.15%).
Figure 2:
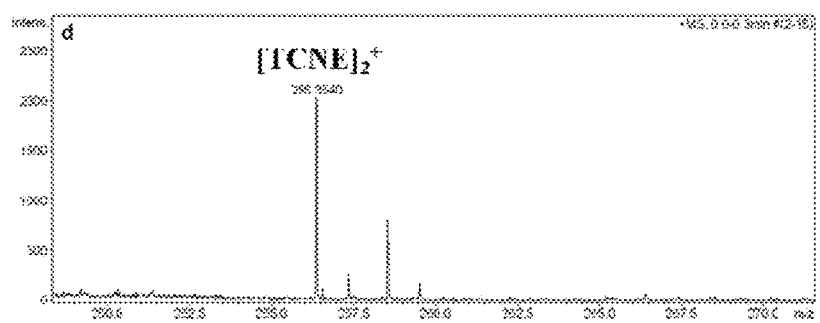
FIG. 2 represents ESI-MS spectra in positive ion mode. 120 h after the preparation of TCNE+TBAB solution in ACTN. A clear signature of dimer formation by [TCNE].$^-$ is present.

The present invention relates to the dimerization of TCNE anion (5 mM) in the organic solvent (acetonitrile) upon aging for 20 hours under static conditions at room temperature, in the presence of anions selected from the group consisting of Br$^-$, Cl$^-$, and SCN$^-$. The anions (Br$^-$, Cl$^-$, SCN$^-$) reduces the TCNE to TCNE anion radical (TCNE.$^-$) which subsequently dimerizes upon aging. The concentration of the anions (Br$^-$, Cl$^-$, SCN$^-$) varied from 0.3 to 4.0 mM. The source for the anions (Br$^-$, Cl$^-$, SCN$^-$) used are tetra-n-butyl ammonium bromide, tetra-n-butyl ammonium chloride and ammonium thiocynate, respectively. In the case of the Br, two different cationic species (tetra-n-butyl ammonium bromide, cetyltrimethylammoniumbromide) as a source were used and do not show any effect of cation on dimerization. The different organic solvents were also used such as acetonitrile, acetone and methyl tetrahydrofuran in amounts ranging from 2 mL to 40 mL. The formation of stable dianionic dimer—[TCNE]$_2^{2-}$ can be scaled up further using higher volume of the solvent and keeping the TCNE concentration same. The formation of [TCNE]2$^2$ in the solution phase at room temperature was confirmed by employing the highly sensitive steady state and time-resolved photoluminescence measurements as shown in FIG. 1, and the signature mass (m/z=256.35) was further confirmed by the electrospray ionization mass spectrometry (ESI-MS) as shown in FIG. 2. It is worth to mention here that method like fluorescence has so far not been exploited as a selective tool for probing radical anion and their dimer.

The novelty of the present invention with respect to the prior art relates to the simple, low cost and one pot process for the formation of stable dianionic dimer-[TCNE]$_2^{2-}$ at room temperature. The formation of [TCNE]$_2^{2-}$ was carried out at different temperatures ranging from 20° C. to 40° C. and the dimerization occurs at room temperature and above.

The new innovation is that the synthesized dianionic $\pi$-dimer-[TCNE]$_2^{2-}$ exhibits highly intense broad emission over the entire visible spectral range (400-800 nm) and opens horizon of a new class of materials to design white LEDs comprising of the single material ($\pi$-[TCNE]$_2^{2-}$), having high intensity over the entire visible spectral range.

There is scarcely any single material that exhibit a broad emission over the visible spectrum, rather white LEDs available typically consist of a blue LED and one or more phosphors to convert part of the blue light to longer wavelengths and suffers from low spectral power distribution in the red region and dampening emission intensity (Pust, P., Schmidt, P. J. & Schnick, W. A revolution in lighting. *Nat. Mater.* 14, 454-458, 2015; US2016240781). Whereas, the $\pi\text{-}[TCNE]_2^{2-}$ formed in this invention opens horizon of a new class of materials to design white LEDs comprising of the single material ($r\text{-}[TCNE]_2^{2-}$), having high intensity over the entire visible spectral range. Further, the $[TCNE]_2^{2-}$ forms electron transfer salts, therefore, it has tremendous potential in a number of crucial applications also such as in molecule-based metals, superconductors, and magnets.

EXAMPLES

Following examples are given by way of illustration of the present invention and therefore should not be construed to limit the scope of the present invention.

Example 1 to 3

Process for the Preparation of $\pi\text{-}[TCNE]_2^{2-}$ Dimer

Example 1

To a well stirred solution of 20 mg of TCNE, 16.7 mg (0.06 mmoles) of TBAC was added in 100 ml either of MTHF in a 100 ml volumetric flask, and allowed to age under ambient conditions up to thirty days.

Example 2

To a well stirred solution of 20 mg of TCNE, 19.3 mg (0.06 mmoles) of TBAB was added in 100 ml either of ACTN in a 100 ml volumetric flask, and allowed to age under ambient conditions up to thirty days.

Example 3

To a well stirred solution of 20 mg of TCNE, 9.1 mg (0.12 mmoles) of ammonium thiocyanate was added in 100 ml acetone in a 100 ml volumetric flask, and allowed to age under ambient conditions up to thirty days.

Example 4

To a well stirred solution of 50 mg of TCNE, either of 38.6 mg (0.12 mmoles) of TBAB, 33.4 mg (0.12 mmoles) of TBAC or 18.2 mg (0.24 mmoles) of ammonium thiocyanate was added in 100 ml either of ACTN, MTHF or acetone in a 100 ml volumetric flask, and allowed to age under ambient conditions up to thirty days.

Example 5

To a well stirred solution of 50 mg of TCNE, 38.6 mg (0.12 mmoles) of TBAB was added in 100 ml ACTN in a 100 ml volumetric flask, and allowed to age under ambient conditions up to thirty days.

Example 6

To a well stirred solution of 50 mg of TCNE, 33.4 mg (0.12 mmoles) of TBAC was added in 100 ml MTHF in a 100 ml volumetric flask, and allowed to age under ambient conditions up to thirty days.

Example 7

To a well stirred solution of 50 mg of TCNE, 18.2 mg (0.24 mmoles) of ammonium thiocyanate was added in 100 ml acetone in a 100 ml volumetric flask, and allowed to age under ambient conditions up to thirty days.

Example 8

To a well stirred solution of 70 mg of TCNE, 57.9 mg (0.18 mmoles) of TBAB was added in 100 ml either of ACTN in a 100 ml volumetric flask, and allowed to age under ambient conditions up to thirty days.

Example 9

To a well stirred solution of 70 mg of TCNE, 50.1 mg (0.18 mmoles) of TBAC was added in 100 ml either of MTHF in a 100 ml volumetric flask, and allowed to age under ambient conditions up to thirty days.

Example 10

To a well stirred solution of 70 mg of TCNE, 27.3 mg (0.36 mmoles) of ammonium thiocyanate was added in 100 ml acetone in a 100 ml volumetric flask, and allowed to age under ambient conditions up to thirty days.

Example 11

To a well stirred solution of 70 mg of TCNE, 1.20 mmoles of tetra $\pi$-butylammoniumbromide (TBAB) was added in 100 ml acetone in a 100 ml volumetric flask, and allowed to age under ambient conditions up to thirty days.

Example 12

Figure 3:
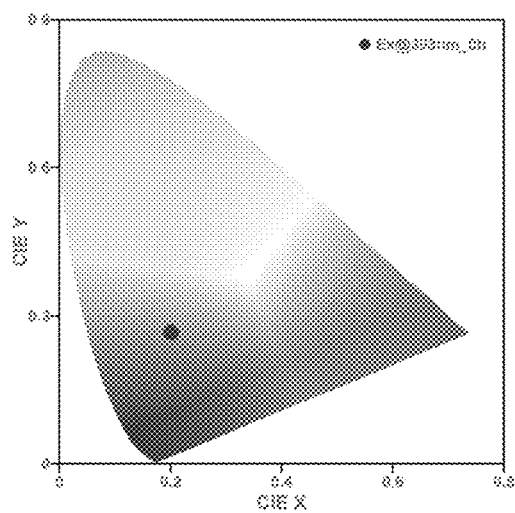
FIG. 3 represents chromaticity plot (0.2, 0.27) of the emission spectrum of TCNE with TBAB just after the solution preparation with the excitation at 393 nm.
Figure 4:
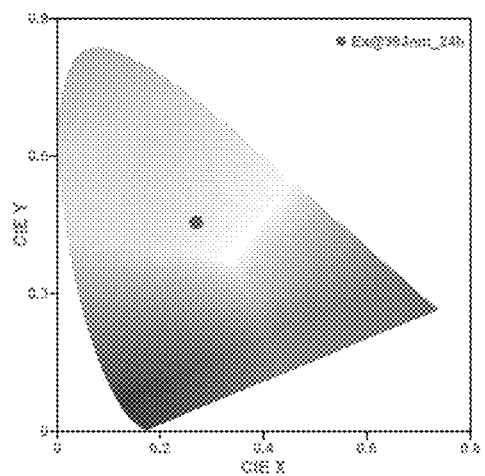
FIG. 4 represents chromaticity plot (0.27, 0.46) of the emission spectrum of TCNE with TBAB 24 hours after the solution preparation with the excitation at 393 nm.
Figure 5:
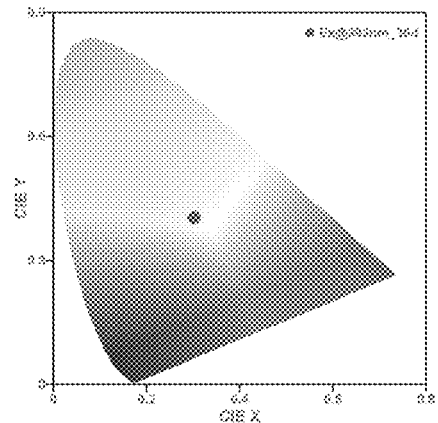
FIG. 5 represents chromaticity plot (0.3, 0.4) of the emission spectrum of TCNE with TBAB 30 days after the solution preparation with the excitation at 393 nm.

The white light emission properties of the synthesized $\pi\text{-}[TCNE]_2^{2-}$ dimer Chromaticity plot of the emission spectrum of TCNE with TBAB (Example 11) just after the solution preparation, 24 hours after the solution preparation and 30 days after the solution preparation with the excitation at 393 nm is shown in FIGS. 3, 4 and 5 respectively.

ADVANTAGES OF THE INVENTION

The main advantages of this invention are:
1. The present investigation illustrates the formation of unconventional stable dianionic dimer $[TCNE]_2^{2-}$ that forms at ambient condition in solution.
2. The process is simple, low cost and one pot and forms dianionic dimer-$[TCNE]_2^{2-}$ at room temperature.
3. This process do not require special equipment and safety devices.
4. It also utilizes the highly sensitive steady state and time-resolved photoluminescence spectroscopy as a tool to demonstrate the florescence property exhibited by the dianionic dimer.
5. The $[TCNE]_2^{2-}$ formed demonstrate highly intense and broad emission over the entire visible spectral range.

6. It opens horizon of a new class of materials to design white LEDs comprising of the single material $[TCNE]_2^{2-}$, having high intensity over the entire visible spectral range.
7. It forms electron transfer salts, therefore, it has tremendous potential in a number of crucial applications also such as in molecule-based metals, superconductors, and magnets.

The invention claimed is:

1. A process for the preparation of a stable dianionic dimer $\pi\text{-}[TCNE]_2^{2-}$ in solution state, wherein TCNE being tetracyanoethylene, the process comprising the steps of:
   i. adding the TCNE in a solvent to obtain a TCNE solution with a weight ratio of 1:20 to 1:100, wherein the anion species source is selected from the group consisting of tetra-n-butyl ammonium bromide [TBAB], cetyltrimethylammoniumbromide [CTAB], tetra-n-butyl ammonium chloride [TBAC], ammonium thiocyanate and combinations thereof;
   ii. adding an anion species source with a concentration range of 1:2 to 1.16 in a solvent to obtain an anion stock solution;
   iii. adding the TCNE solution obtained in step (i) in the anion stock solution obtained in step (ii) with a final concentration ratio of the TCNE and the anion species ranging from 3:1 to 27:1; and
   iv. aging the solution obtained in step (iii) for a period in the range of 20 hours to 30 days at room temperature in the range of 20 to 40° C. to obtain the stable dianionic dimer $\alpha\text{-}[TCNE]_2^{2-}$, wherein the stable dianionic dimer $\pi\text{-}[TCNE]2^{2-}$ forms electron transfer salts, and wherein the stable dianionic dimer $\pi\text{-}[TCNE]2^{2-}$ forms new molecule-based metals, superconductors, and magnets.

2. The process as claimed in claim 1, wherein the solvent in step (i) is an organic solvent selected from the group consisting of acetonitrile (ACTN), acetone, 2-methyl tetrahydrofuran (MTHF) and combinations thereof.

3. The process as claimed in claim 1, wherein the stable dianionic complex $\pi\text{-}[TCNE]_2^{2-}$ exhibits a highly intense broad emission over the entire visible spectral range (400-800 nm), which further intensifies with aging time in the range of 20 hours to 30 days.

4. The process as claimed in claim 3, wherein the stable dianionic dimer $\pi\text{-}[TCNE]_2^{2-}$ exhibits intense white light emission with chromaticity coordinates ranging from 0.20, 0.27 to 0.3, and 0.46, and wherein the stable dianionic dimer $\pi\text{-}[TCNE]2^{2-}$ is tunable by changing the solvent.

* * * * *